(12) United States Patent
Hughes et al.

(10) Patent No.: US 8,527,212 B2
(45) Date of Patent: Sep. 3, 2013

(54) INCREASED ABSORPTION-MEASUREMENT ACCURACY THROUGH WINDOWING OF PHOTON-TRANSIT TIMES TO ACCOUNT FOR SCATTERING IN CONTINUOUS WEBS AND POWDERS

(75) Inventors: Michael Kon Yew Hughes, Vancouver (CA); Sebastien Tixier, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 304 days.

(21) Appl. No.: 13/027,259

(22) Filed: Feb. 14, 2011

(65) Prior Publication Data

US 2012/0209536 A1  Aug. 16, 2012

(51) Int. Cl.
*G06F 19/00* (2011.01)
*G01N 21/35* (2006.01)

(52) U.S. Cl.
USPC ............. 702/28; 250/571; 250/339; 250/559; 356/429; 356/51

(58) Field of Classification Search
USPC .......................................................... 702/28
See application file for complete search history.

(56) References Cited

U.S. PATENT DOCUMENTS

| | | | |
|---|---|---|---|
| 4,786,817 A * | 11/1988 | Boissevain et al. | 250/559.01 |
| 5,945,676 A | 8/1999 | Khalil et al. | |
| 6,070,583 A | 6/2000 | Perelman et al. | |
| 6,342,701 B1 * | 1/2002 | Kash | 250/458.1 |
| 6,960,769 B2 * | 11/2005 | Burk et al. | 250/339.07 |
| 7,199,884 B2 | 4/2007 | Jasinski et al. | |
| 7,298,492 B2 | 11/2007 | Tixier | |
| 7,321,425 B2 | 1/2008 | Haran | |
| 7,382,456 B2 | 6/2008 | Tixier et al. | |
| 7,528,958 B2 | 5/2009 | Hughes et al. | |
| 7,626,171 B2 | 12/2009 | Cooke et al. | |
| 7,847,943 B2 | 12/2010 | Hellstrom | |
| 8,187,424 B2 * | 5/2012 | Haran et al. | 162/198 |
| 2007/0260145 A1 | 11/2007 | Heanue et al. | |
| 2009/0128799 A1 | 5/2009 | MacHattie et al. | |
| 2012/0049070 A1 * | 3/2012 | Mousavi et al. | 250/341.8 |

OTHER PUBLICATIONS

Author: Michael Wahl, Title: Time-Correlated Single Photo Counting, Date: 2009, Publisher: PicoQuant GmgH, Edition or Volume: Technical Note: TCSPC v.2.1.*
PCT/CA2012/00120 International Search Report dated May 14, 2012.
Svensson of al., Near—infrared photon time-of-flight spectroscopy of turbid materials up to 1400 nm, Review of Scientific Instruments 80, 063105, 2009.

(Continued)

*Primary Examiner* — Tung S Lau
*Assistant Examiner* — Stephanie Chang
(74) *Attorney, Agent, or Firm* — Cascio Schmoyer & Zervas

(57) ABSTRACT

Radiation scattering is one of the main contributors to the uncertainty of near infrared (NIR) measurements. Enhanced absorption-measurement accuracy for NIR sensors is achieved by using a combination of NIR spectroscopy and time-of-flight techniques to select photons that are the result of a given mean free path within a moving sample target. By measuring absorption as a function of path length or by windowing signals that are attributable to excessive scattering of NIR radiation within the sample, this technique affords the calculation of more accurate and more universal calibrations. The NIR sensor employs short or ultra-short laser pulses to create NIR that is directed to the moving sample and emerging radiation is detected over time. Windowing effectively truncates non-contributing measurements.

24 Claims, 4 Drawing Sheets

(56) References Cited

OTHER PUBLICATIONS

Jerszy Plucinski, Opical Time-of-Flight Spectroscopy for highly scattering materials measurements, Proceedings of the SPIE vol. 14, 5064 2003 pp. 69-74.

Beck & Hicki GMBH Specification Sheet for SPC-154 4 Channel TCSPC Module Jul. 2009.

Newport Technology, Supercontinuum Generation in SCG-800 Photonic Crystal Fiber, information sheet, Feb. 14, 2011.

Edinburgh Instruments Ltd., What is TCSPC, Technical Note, From www.edinst.com pp. 1-4, Feb. 14, 2011.

Edinburgh Instruments Ltd., Why TCSPC for Fluorescence Lifetime Measurements, Technical Note, From www.edinst.com pp. 1-2, Feb. 14, 2011.

\* cited by examiner

INCREASED ABSORPTION-MEASUREMENT ACCURACY THROUGH WINDOWING OF PHOTON-TRANSIT TIMES TO ACCOUNT FOR SCATTERING IN CONTINUOUS WEBS AND POWDERS

FIELD OF THE INVENTION

The present invention generally relates to scanning sensors that employ near infrared radiation for detecting the presence of specific components in paper, plastic, powders and like products on a continuous basis. In particular, the sensors employ windowing or time-correlated single-photon detection techniques that reduce the adverse effects of scattering on absorption measurements.

BACKGROUND OF THE INVENTION

Various sensor systems have been developed for detecting sheet properties "on-line," i.e., on a sheet-making machine while it is operating. Sensors for continuous flat sheet production processes typically employ single or dual-sided packages with on-line sensors that traverse or scan traveling webs of sheet material during manufacture. Near infrared (NIR) spectroscopy is the method of choice for measuring composition or component weight and moisture content in a multitude of products. These include materials produced in sheets such as paper and plastic. The technique is fast, inexpensive, and is compatible with on-line measurement, which allows the process to be controlled in a closed-loop fashion. NIR spectroscopy is accurate if a suitable calibration model can be obtained for the product to be measured. A specific calibration model is required for two main reasons. One reason is that a number of overlapping absorption bands exists in the NIR. Typically, a number of components in the product contribute to the measured absorption bands and a model is required to separate the contributions from the individual components. The second reason is related to light scattering: when light interacts with a sample it gets absorbed and scattered and the amount of scattering depends on the chemical as well as the structural properties of the sample. Paper, in its simplest form, is a mixture of cellulose fibers surrounded by air. Due to index of refraction changes, the cellulose/air interfaces lead to significant light scattering. The scattering power of paper can change dramatically as fillers or even moisture fill the gaps between the cellulose fibers thereby displacing the air. Scattering affects the NIR absorption technique through changes in the average path length through the sample. Scattering, especially in products like paper and powder samples, can significantly reduce the accuracy of absorption-type measurements due to changes in the photon mean free path. As calibrations are not only dependent on a single component but on many components in a non-linear fashion, calibration curves cannot be simply computed. For example, the calibration curves for measuring moisture in paper are multidimensional and depend on cellulose, ash, and furnish contents and concentrations. Simpler calibrations would greatly assist end users by improving the accuracy and robustness of on-line measurements.

SUMMARY OF THE INVENTION

The present invention is based, in part on the recognition that increased absorption-measurement accuracy for near infrared (NIR) sensors can be achieved by using a combination of near infrared spectroscopy and time-of-flight techniques to select photons that are the result of a given mean free path within the target. In particular, measurements of absorption as a function of path length are conducted and by fitting a model that correlates the absorption and the scattering of NIR in the target to the data, scattering-free absorption measurements are obtained. Alternatively, an average absorption per unit path length can be calculated from the data. The average absorption normalized by unit path length is by definition free of the scattering contribution.

In another embodiment, the signals that are attributable to excessive or minimal scattering of NIR radiation within the sample of interest are removed through windowing. Another possible technique is referred to as time-correlated single-photon counting (TCSPC) where the processor operates by measuring the arrival time of every photon as represented by electrical detection signals and uses an algorithm to determine at least one property of the material being monitored. TCSPC is particularly useful where there are restraints to the intensity that can be employed and is more accurate for shorter pulses or for targets where the maximal amount of scattering is less.

These techniques afford the calculation of more accurate and more universal calibrations. As scattering is one of the main contributors to the uncertainty of NIR measurements, the inventive method of extracting the effects of scattering produces more accurate absorption measurements. To remove the effects of scattering, the inventive NIR sensor employs short or ultra-short light pulses and a way of discriminating the measurements by time-of-flight. As described above, the technique can be implemented by modeling the absorption measurements to calculate the scattering, by calculating an average absorption per unit path length or by measuring absorption of the photons that are selected for their similar path lengths or time-of-flight through the sample composition.

Accordingly, in one aspect, the invention is directed to a sensor for measuring at least one property of a composition of a moving sample that includes:

a light source, which emits broadband optical pulses at a sample of the composition;

a receiver operable to detect reflected or transmitted radiation from the sample and to provide electrical detection signals;

synchronization means for receiving electrical pulses from the light source or optical pulses from the receiver and for providing electrical synchronization signals to a processor; and a processor that receives the electrical detection signals and the electrical synchronization signals and that is operable to determine at least one property of the composition with substantial independence of the measurement from the effects associated with scattering in the composition.

In another aspect, the invention is directed to a system for continuous on-line measurement of a characteristic of a moving sample that includes:

a broadband light source, which emits optical pulses, operable for emitting pulsed radiation at the moving sample, wherein the ultrafast light source travels over the cross direction of the moving sample;

a receiver operable to detect reflected or transmitted radiation from the sample and provide electrical detection signals and wherein the receiver travels over the cross direction of the moving sample;

synchronization means for receiving electrical pulses from the light source or optical pulses from the receiver and for providing electrical synchronization signals to a processor; and a processor that receives the electrical detection signals and the electrical synchronization signals and that is operable to determine at least one property of the composition with substantial independence of the measurement from the effects associated with scattering in the composition.

In yet another aspect, the invention is directed to a method of measuring at least one property of a moving sample that includes the steps of:

(a) directing radiation at the moving sample;

(b) measuring reflected or transmitted radiation from the sample and generating electrical signals therefrom; and (c) determining at least one property of the sample from the electrical signals whereby electrical signals associated with scattering within the sample are processed with the knowledge or consideration that scattered photons have longer transit times.

DESCRIPTION OF PREFERRED EMBODIMENTS

Figure 1:
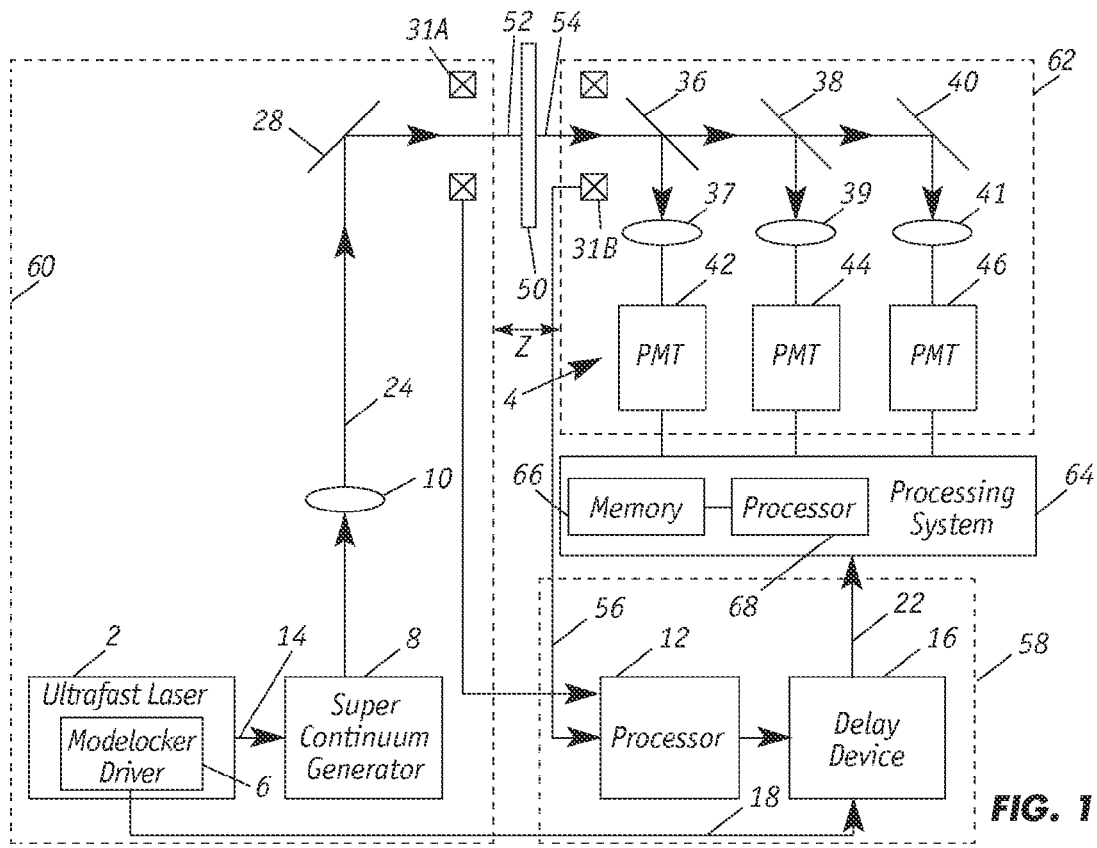
FIGS. 1 and 3 illustrate scanning NIR sensor systems employing time-correlated single-photon counting.

FIG. 1 shows the structure of a NIR sensor apparatus for monitoring at least one property of the moving sheet or web of material 50. The NIR sensor is particularly suited for measuring properties of continuous web materials such as sheets of paper or plastic. The sensor can also be readily adapted to measure a continuous stream of discrete materials, such as powder compositions, that is conveyed past the sensor. The sensor generates NIR radiation 52 that is directed to material 50 and measures the radiation that emerges therefrom using time-correlated single-photon counting (TCSPC). The principle of TCSPC is the detection of single photons and the measurement of their arrival times with respect to a reference signal, usually a light source. TCSPC is a statistical method and a high repetitive light source is employed to accumulate a sufficient number of photon events for a required statistical data precision. For example, a light source can be employed to generate both the (i) reference light pulses that are converted to references electronic (reference) pulses and (ii) sample light pulses that are directed to a sample target. Single photons emerging from the sample are converted to single photon (signal) pulses. The TCSPC electronics can be viewed as receiving two inputs, with the electronics being initiated when it receives a reference pulse and the electronics being stopped by the signal pulse. The time interval is measured. The intensity of the measured photon is not critical aside from discriminating against double count events; it is the timing of the signals that is of importance. TCSPC uses intensity filters, for example, to reduce the photon intensity to a level where the probability of a photon being detected by each detector from each pulse is substantially less than unity. This is then timed to a 'zero scattering' photon. With many pulses a curve that contains much information is generated and from which analysis yields additional and more complex measurements. TCSPC is further described in "Advanced Time-Correlated Single Photon Counting Techniques," Becker, W., Springer (2005); *Time correlated single-photon counting (TCSPC) using laser excitation*, Phillips, D.; Drake, R. C.; O'Connor, D. V.; Christensen, R. L. Source: *Analytical Instrumentation*, v 14, n 3-4, p 267-292, September-December 1985 and U.S. Pat. No. 6,342,701 to Kash, which are incorporated herein by reference.

In particular, the NIR sensor includes an ultrafast laser 2, which produces laser pulses 14, and that is coupled to a supercontinuum generator 8. For example, a pulsed laser source that is coupled to a nonlinear fiber can generate supercontinuum light pulses 24 over the desired wavelength range. The required duration of supercontinuum light pulses 24 depends on the amount of scattering. For paper samples, it is expected that the detected pulses be about 200 ps in length, requiring input light pulses of about 1 ps in duration. For such requirements, a preferred laser is an ultrafast modelocked laser with supercontinuum generation. However, if the NIR sensor is to measure only one or two wavelengths, such as for a moisture measurement in paper, the required wavelengths can also be generated by non-linear wavelength mixing and other means. NIR radiation 24 is focused by objective lens 10 and directed by mirror 28 into moving sheet 50. Instead of traveling through free space, in some applications, radiation can be launched into and transmitted through a delivery fiber optic cable or optical fiber.

In this embodiment, receiver 4 is configured as a three-channel NIR detector for measuring three properties in material 50 and from these properties other characteristics, such as moisture content, can be derived. Receiver 4 includes dichroic mirrors or optical filters 36, 38 and 40 and corresponding detectors 42, 44 and 46. Each dichroic beam splitter is configured for high transmissivity for certain parts of the radiation spectrum and/or high reflectivity in certain other parts of the radiation spectrum. Each detector 42, 44 and 46 can comprise a photomultiplier tube (PMT) or other fast optical detector or photodetector. Optionally, separate infrared band pass filters and/or intensity filters 37, 39, and 41 can be positioned before detectors 42, 44, and 46, respectively; in this fashion, each detector measures the intensity of only the portion of the NIR beam spectrum that falls within the band pass of the associated filter. When both band pass and intensity filters are employed, the intensity filter can be positioned immediately downstream of the band pass filter. Each PMT detector 42, 44 and 46 captures selected regions of NIR 54 that emerges from moving sheet 50. Each detector generates output electrical detection signals corresponding to the intensity of photons measured. A spectrometer can be employed instead of the optical filters (dichroic) and associated individual detectors.

The gap or displacement distance "z" between sensor heads 60, 62 through which the sample traverses can vary particularly when the dual sensors are in motion as part of a scanner. To account for this z "wander," the gap separation can be continuously measured. Dynamic measurements can be achieved with conventional devices, such as, for example, a displacement sensor, that employs inductive or magnetic measuring device 31A, 31B, which is described in U.S. Pat. No. 7,199,884 to Jasinski et al., which is incorporated herein by reference. Distance signals 56 from z measurements are communicated to processor 12 that calculates the time delay based on the z measurements and generates time delay signals to delay device 16.

In this embodiment, the source of NIR radiation also provides the synchronizing signals so that the steps of directing radiation to the sample and measuring reflected or transmitted radiation from the sample are synchronized as part of the process of measuring absorption as a function of time-of-flight. Synchronization signal 18 is generated by a mode locker driver 6 of the laser 2 and is directed to electrical delay device 16 to take into account of (and corrected for) the z wander during scanning. Other devices, such as an in-built photodiode, can be employed to generate this signal. Electronic delay device 16, which delays synchronization signal 18, is configured to provide electrical synchronization signals 22 to processing system 64 to effectively switch on NIR receiver 4 in a synchronous detection scheme.

The outputs from detectors 42, 44, and 46 are electrical signals that initiate the TCSPC electronics. For example, a signal processing system 64 is coupled to detectors 42, 44, and 46 to receive the electrical detection signals. The signal processing system 64 comprises a memory 66 for storing calibration and normalization data to permit calculation of the moisture content, caliper or basis weight in the case where material 50 is paper. Signal processing system 64 also includes processing electronics and a processor or analyzer 68, such as a digital signal processor, that receives processed electrical signals (amplified, filtered and converted to a digital signal) from the processing electronics. The processor 68 combines the signals received to determine at least one property of the material. For example, the processor operates by measuring the arrival time of every detected photon as represented by the electrical detection signals and uses an algorithm to determine at least one property of material 50 with substantial independence of the measurement from the effects associated with scattering in the composition.

As shown in FIG. 1, when operating in the transmissive mode, the light source that includes the ultrafast laser 2 and supercontinuum generator 8 can be housed in sensor head 60 and NIR receiver 4 can be housed in sensor head 62 that is on the opposite side of material 50. The NIR sensor can also operate in the reflective mode, in which case, both NIR source and receiver are positioned on the same side as material 50. Typically, the remaining components of the NIR sensor, such as processor 12 and electrical delay device 16, are housed in module 58 that can be located remotely from the sensor heads.

Figure 2:
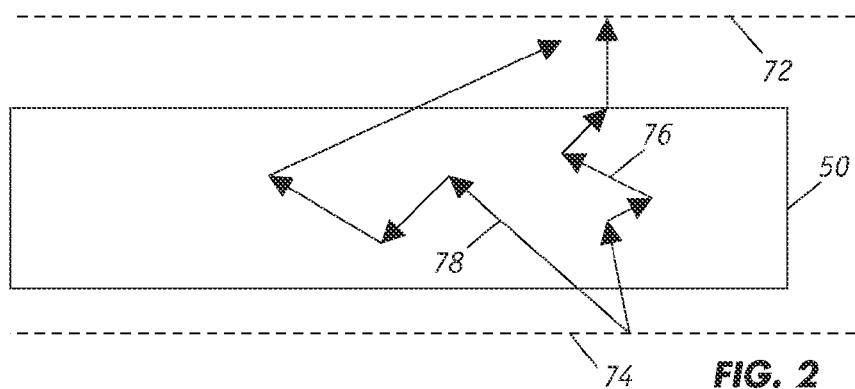
FIG. 2 is a depiction of the photon paths through a sample.

FIG. 2 depicts sample 50 that is positioned within a measurement gap that is defined by surfaces 72, 74 of two oppositely facing sensor heads. NIR 76 that is directed to sample 50 from a NIR source (not shown) interacts with components within the sample before exiting the sample and being detected in NIR receiver (not shown). A portion of the radiation will be absorbed and scattered. The degree of scattering in the sample depends on, among other things, the composition of the sample, temperature, and wavelength of the NIR. Highly scattered radiation 78 remains in the sample a longer period of time before exiting. Radiation 76 and 78 are arbitrarily shown to experience an identical number of scattering events. The highly scattered radiation 78 could experience a number of scattering events significantly larger than that of radiation 76.

In operation of the NIR sensor, the system preferably undergoes an initial standardization procedure with respect to the material being monitored. In one standardization technique, with the sensor in the "off-sheet" mode so that no product is in the measurement gap of the sensor, a flag that consists of a thin layer of PTFE (TEFLON) or aluminum oxide ($Al_2O_3$) is inserted into the gap between the NIR source and receiver. Thereafter, the NIR sensor is activated and the integrated photon counts at all NIR wavelengths of interest over a fixed delay time period are recorded. The ratio of the integrated photon counts at time zero over the now integrated photon counts yields a standardized correction value for each wavelength. The correction value is applied to normalize each subsequent measurement in order to correct for variations in the radiation source, gap alignment and other operating parameters. Another standardization technique is to use a flag that has the appropriate physical properties in term of density, thickness and composition so that it contains path lengths that are similar to those in the material to be measured. Thereafter, the instrumental function is measured at all NIR wavelengths of interest. The ratio of the instrument functions at time zero with the now instrumental functions yields a standardized correction value that can be applied to subsequent measurements. As all the detectors have different optical paths, the standardization signal can be used to synchronize the different detection channels.

Figure 3:
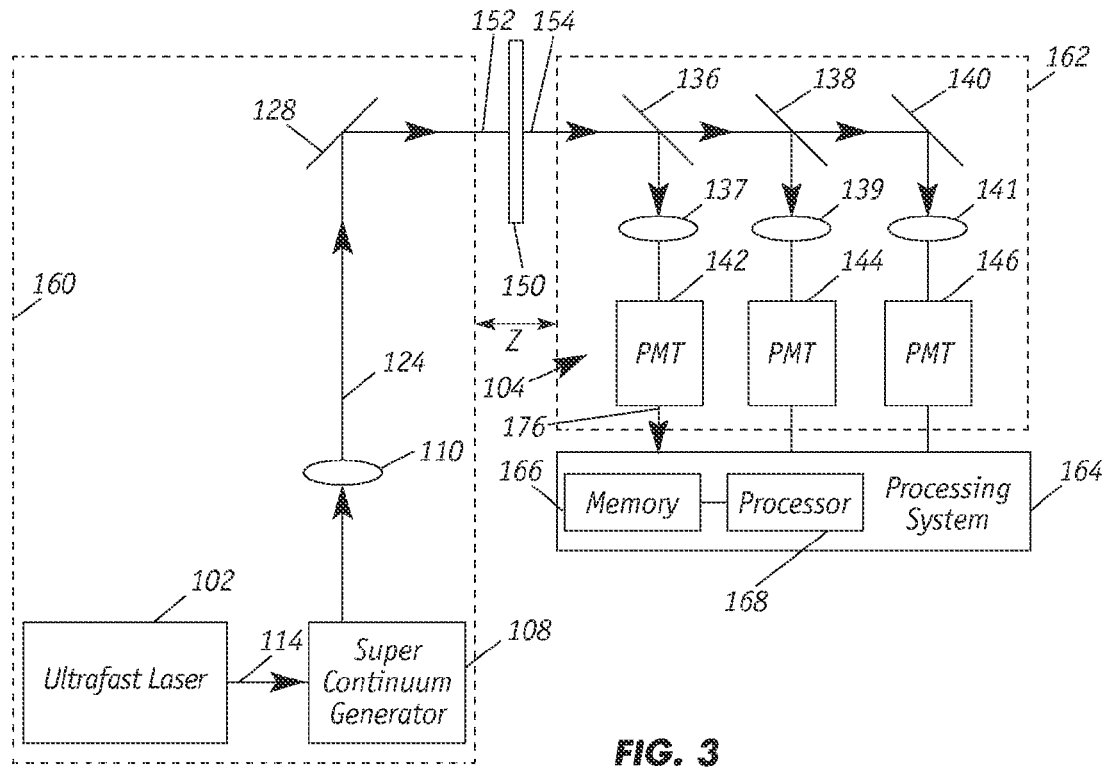

FIG. 3 shows another structure of a NIR sensor apparatus using time-correlated single-photon counting wherein the synchronization signals are generated by a fast photodetector within the receiver. Supercontinuum light 124 is generated by a pulsed laser source 102, which produces laser pulses 114, and that is coupled to a supercontinuum generator (nonlinear fiber) 108. NIR radiation 124 is focused by objective lens 110 and radiation 152 is directed by mirror 128 into moving sheet 150. Receiver 104 is configured as a two-channel NIR detector and includes dichroic mirrors or optical filters 136, 138 and 140 and corresponding detectors 142, 144 and 146. Each detector can comprise a photomultiplier tube or other fast photodetector. Separate infrared band pass and/or intensity filters 137, 139, and 141 are optionally positioned before detectors 142, 144, and 146, respectively. Each detector 144 and 146 captures selected regions of NIR 154 that emerges from moving sheet 150. Each detector generates output electrical detection signals corresponding to the intensity and timing of photons measured. Ultrafast laser 102 and supercontinuum generator 108 can be housed in sensor head 160 and receiver 104 can be housed in sensor head 162.

Fast optical detector or photodetector 142, which is responsive to the earliest transmitted photons, generates synchronizing signals 176 to take into account the head movement so no displacement sensor is required to measure the gap distance "z" between sensor heads 160, 162. Synchronization signal 176 is directed to processing system 164 to synchronize detectors 144 and 146, which collectively measure two properties of material 150 using memory 166 and processor 168.

Figure 4:
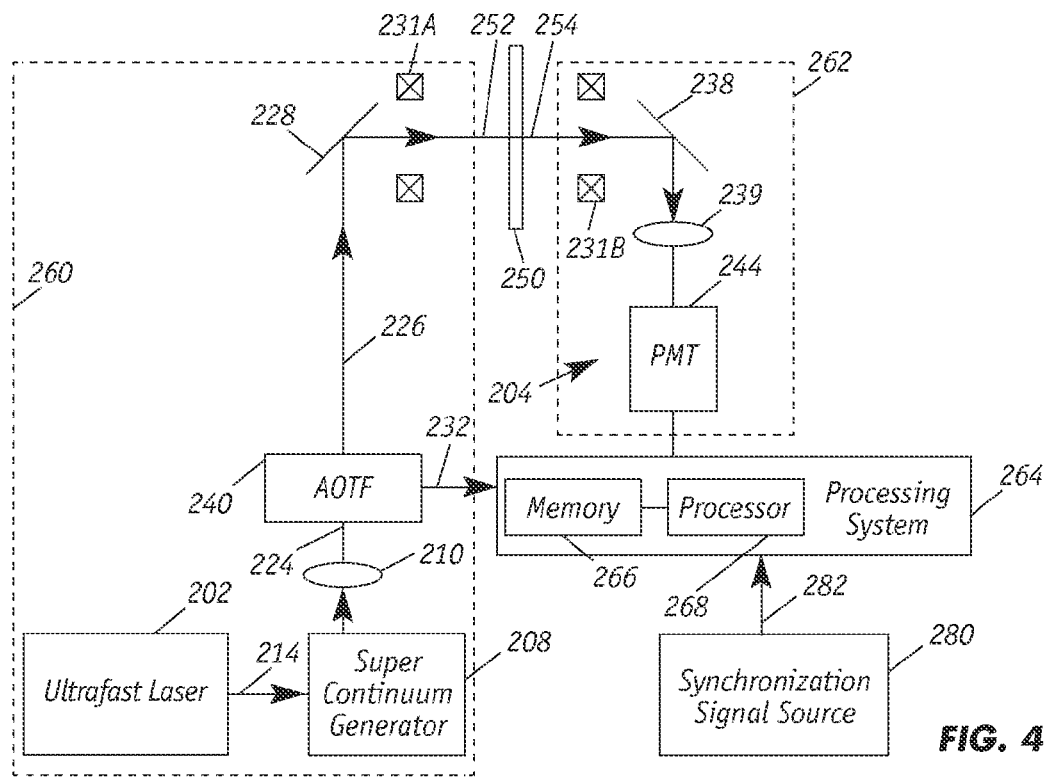
FIG. 4 illustrates a scanning NIR sensor system employing an acousto-optic tunable filter.

FIG. 4 shows the structure of a NIR sensor that employs an acousto-optic tunable filter (AOTF) light source and time-correlated single-photon counting. Instead of using an AOTF, a micro-mirror array and appropriate optics can be used as the tunable grating. Moreover, other technologies such as liquid crystal tunable filters can also be used. As an alternative to the configurations of the NIR sensors as shown in FIGS. 1 and 3 in which broadband light is directed through a material, light can be dispersed so that only a discrete wavelength is allowed through by use of an AOTF. In this case, light will scatter in the material being measured and the time of arrival at the receiver will be a strong function of the amount of scattering. This technique, which executes measurements in series or sequentially, may be slower than those depicted in FIGS. 1 and 3 which execute the measurements in parallel.

As illustrated, broadband light 224 is generated by a pulsed laser source 202, which produces laser pulses 214, and that is coupled to a supercontinuum generator (nonlinear fiber) 208. NIR radiation 224 is focused by objective lens 210 into AOTF 240. Each pulse 226, which is generated by the broadband source 208, is filtered by AOTF 240 so that only one narrow wavelength band 226 is generated at a time and directed by minor 228 into moving sheet 250. As AOTF 240 receives and filters pulse 226, AOTF 240 generates corresponding wavelength information 232 to processing system 264. Receiver 204 includes mirror 238 that directs radiation 254 emerging from material 250 through filter 239 and into PMT or fast photodetector 244. PMT 244 generates output electrical detection signals corresponding to the intensity and timing of photons measured. Synchronization signals 282 which are illustrated as being derived from source 280 can be generated by the laser and then delayed by an electronic delay box that is controlled by a z sensor as illustrated in FIG. 1 or it can be generated by a fast photodetector as illustrated in FIG. 3. In this regard, z-direction sensor 231A, 231B is employed in the former synchronization scenario. A signal processing system 264, which is coupled to detector 244, receives the electrical detection signals and comprises a memory 266 a processor or analyzer 268.

While AOTF 240 is illustrated in FIG. 4 as being configured to direct filtered radiation 252 into material 250, the AOTF can also be positioned downstream of material 250. In this case, the AOTF filters the broadband radiation that emerges from the material and directs a narrow wavelength band into the photodetector. Ultrafast laser 202 and supercontinuum generator 208 can be housed in sensor head 260 and receiver 204 can be housed in sensor head 262.

Figure 5:
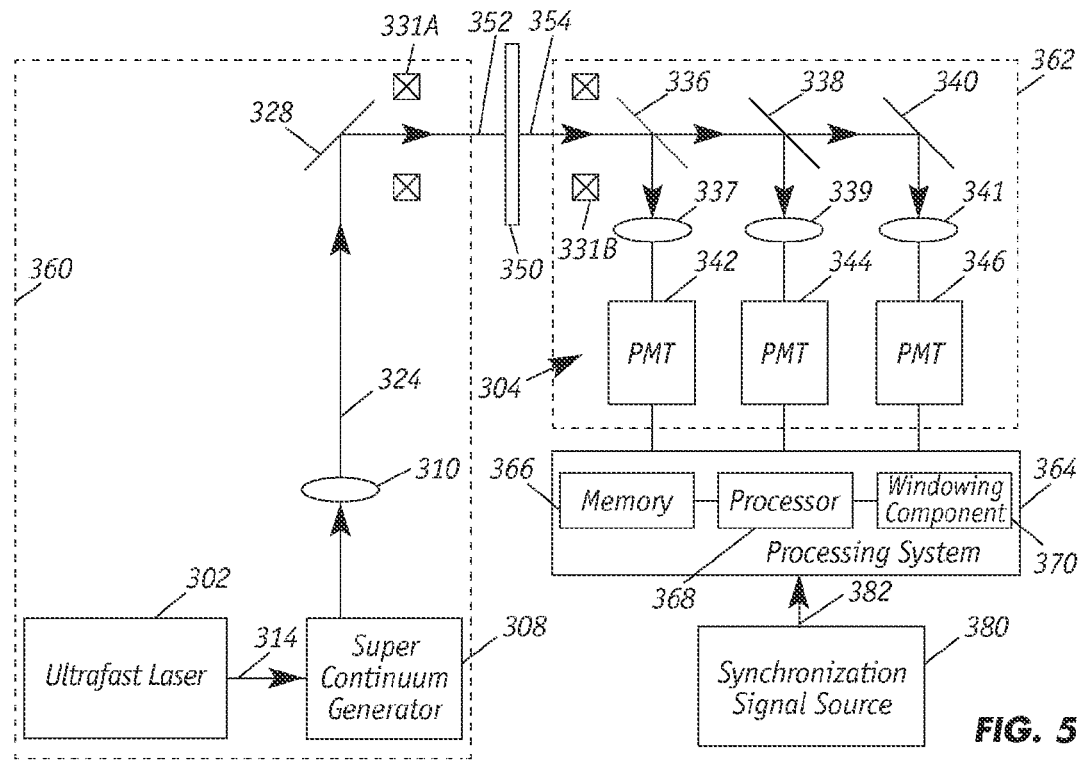
FIG. 5 illustrates a scanning NIR sensor system employing windowing.

FIG. 5 shows the structure of a NIR sensor apparatus wherein NIR radiation 353 is directed to a material and the radiation 354 that emerges therefrom is analyzed with windowing techniques. Supercontinuum light 324 is generated by a pulsed laser source 302, which produces laser pulses 314, and that is coupled to a supercontinuum generator (nonlinear fiber) 308, which can be housed in sensor head 360. Supercontinuum light can also be generated by other well-known means. NIR radiation 324 is focused by objective lens 310 and directed by mirror 328 into moving sheet 350. Receiver 304, which can be housed in sensor head 362, includes dichroic mirrors or optical filters 336, 338 and 340 and corresponding PMT or fast photodetectors 342, 344 and 346. Separate infrared band pass filters 337, 339, and 341 are optionally positioned before detectors 342, 344, and 346, respectively. Each detector generates output electrical detection signals corresponding to the intensity and timing of photons measured.

Synchronization signals 382 which is illustrated as being derived from source 380 can be generated by the laser and then delayed by an electronic delay box that is controlled by a z displacement sensor as illustrated in FIG. 1 or it can be generated by a fast photodetector as illustrated in FIG. 3. In this regard, z-direction sensor 331A, 331B is employed in the former synchronization scenario. A signal processing system 364, which is coupled to detectors 342, 344 and 346, receives the electrical detection signals and comprises a memory 366 a processor or analyzer 368. To enhance the absorption-measurement accuracy of the NIR sensor, a windowing component 370 is implemented to window the photon-transit times to account for NIR scattering. The processor 368 combines the signals received to determine at least one property of the material through windowing whereby the processor gates the electrical detection signals to eliminate signals outside a fixed time window relative to the synchronization pulses and uses an algorithm to determine at least one property of material 350 with substantial independence of the measurement from the effects associated with scattering in the composition.

Figure 6:
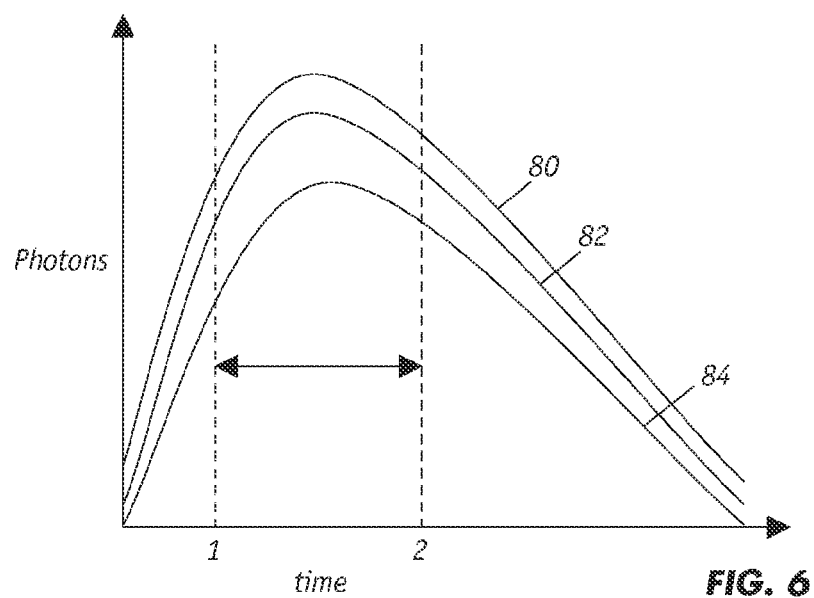
FIG. 6 is a graph of photons vs. transit time measured at different wavelengths.

FIG. 6 illustrates time-of-flight measurements at three different NIR regions as measured by the NIR sensor. In particular, the intensity (or number) of photons emerging from a sample over time at three NIR regions, as represented by curves 80, 82, and 84, was measured. NIR that is first detected corresponds to that which passes through the sample with minimal interaction and therefore with the shortest path lengths in the sample whereas highly scattered NIR is detected later. It is expected that the degree of scattering will be a function of NIR wavelength. The windowing component selects points that correspond to a range of path lengths in the sample so as to exclude points with excessive scattering as well as points that correspond to insufficient interaction. With the components in the material. As shown, this technique effectively truncates the two-outer portions of the curves for measurements. The selection of the points of demarcation will depend on the shape of the curves with the goal of enhancing absorption-measurement accuracy. In other words, processor 368 initiates and stops measurements so that only the photons arriving between times 1 and 2 in the graph are integrated.

Figure 7:
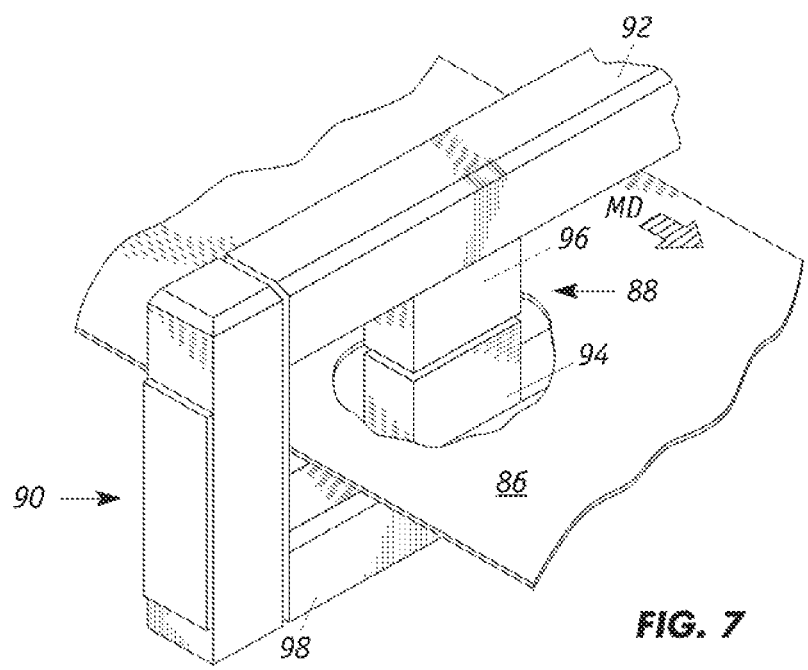
FIG. 7 shows a sheet making system implementing the NIR sensor.

FIG. 7 illustrates one particular implementation of the NIR sensor whereby the sensor is incorporated into a dual head scanner 88 of scanner system 90 that is employed to measure properties of paper or polymer in films in a continuous production process. Upper scanner head 96, which houses the NIR source, and lower scanner head 94, which houses the NIR receiver, move repeatedly back and forth in the cross direction across the width of the moving sheet 86, which moves in the machine direction (MD), so that the characteristics of the entire sheet may be measured. Scanner 88 is supported by two transverse beams 92, 98, on which are mounted upper and lower scanning heads 96, 94. The operative faces of the lower and upper scanner heads 94, 96 define measurement gap that accommodates sheet 86. The lower scanner head 94 may include a sheet stabilization system such as an air-bearing stabilizer (not shown) to maintain the sheet on a consistent plane as it passes through the measurement gap. The movement of the dual scanner heads 94, 96 is synchronized with respect to speed and direction so that they are aligned with each other.

A technique of measuring powdered materials is to use a conveyer to continuously present the materials to a sensor of the presenting invention that is operating in the reflective mode. With a conveyer belt of limited width, sampling across the belt would not be necessary and a single stationary, point measurement may suffice. Alternatively, stationary, multiple point measurements can be implemented.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims

What is claimed is:

1. A sensor for measuring at least one property of a composition of a moving sample that comprises:
   a light source, which emits broadband optical pulses at the moving sample of the composition;
   a receiver operable to detect reflected or transmitted radiation from the moving sample and to provide electrical detection signals wherein the distance between the light source and receiver varies;
   synchronization means for receiving electrical pulses from the light source or optical pulses from the receiver and for providing electrical synchronization signals to a processor; and wherein the processor receives the electrical detection signals and the electrical synchronization signals and is operable to determine at least one property of the composition with independence of the measurement from the effects associated with scattering in the composition and wherein the processor measures the arrival time of photons as represented by the electrical detection signals.

2. The sensor of claim 1 wherein the synchronization signal is generated at the receiver by a fast optical detector that is responsive to the earliest transmitted or reflected photons from the composition.

3. The sensor of claim 1 wherein the synchronization signal is generated by the light source.

4. The sensor of claim 3 wherein the receiver is configured to detect transmitted radiation from the moving sample and wherein the light source and the receiver are on opposite sides of the moving sample and the synchronization signal is corrected to account for the distance between the source and the receiver as measured by a displacement sensor.

5. The sensor of claim 1 wherein the receiver comprises a multi-channel detector that includes a plurality of beam splitters, a plurality of intensity filters and a plurality of band pass filters with corresponding single element detectors.

6. The sensor of claim 1 wherein the receiver is configured to detect transmitted radiation from the moving sample and the sensor further comprises a first sensor head housing the light source and from which pulsed radiation directed at the sample is emitted (ii) a second sensor head housing the receiver and (iii) means for measuring the distance between the first and second sensor heads and for generating distance signals to the synchronizing means.

7. The sensor of claim 1 wherein the light source emits near-infrared radiation.

8. The sensor of claim 1 wherein the receiver is operable to detect reflected radiation from the moving sample.

9. The sensor of claim 1 wherein the light source travels over a cross direction of the moving sample and the receiver travels over the cross direction of the moving sample.

10. The sensor of claim 1 wherein the moving sample comprises paper, plastic or powdered products.

11. A sensor for measuring at least one property of a composition of a moving sample that comprises:
    a light source, which emits broadband optical pulses at a moving sample of the composition;
    a receiver operable to detect reflected or transmitted radiation from the moving sample and to provide electrical detection signals wherein the distance between the light source and receiver varies;
    synchronization means for receiving electrical pulses from the light source or optical pulses from the receiver and for providing electrical synchronization signals to a processor; and
    wherein the processor receives the electrical detection signals and the electrical synchronization signals and is operable to determine at least one property of the composition with independence of the measurement from the effects associated with scattering in the composition and wherein the processor gates the electrical detection signals to eliminate signals outside a fixed time window relative to the synchronization pulses.

12. The sensor of claim 11 wherein the synchronization signal is generated at the receiver by a fast optical detector that is responsive to the earliest transmitted or reflected photons from the composition.

13. The sensor of claim 11 wherein the synchronization signal is generated by the light source.

14. The sensor of claim 13 wherein the receiver is configured to detect transmitted radiation from the moving sample and wherein the light source and the receiver are on opposite sides of the moving sample and the synchronization signal is corrected to account for the distance between the source and the receiver as measured by a displacement sensor.

15. The sensor of claim 11 wherein the receiver comprises a multi-channel detector that includes a plurality of beam splitters, a plurality of intensity filters and a plurality of band pass filters with corresponding single element detectors.

16. The sensor of claim 11 wherein the receiver is configured to detect transmitted radiation from the moving sample and the sensor further comprises (i) a first sensor head housing the light source and from which pulsed radiation directed at the sample is emitted (ii) a second sensor head housing the receiver and (iii) means for measuring the distance between the first and second sensor heads and generating distance signals to the synchronizing means.

17. The sensor of claim 11 wherein the light source emits near-infrared radiation.

18. The sensor of claim 11 wherein the receiver is operable to detect reflected radiation from the moving sample.

19. The sensor of claim 11 wherein the light source travels over a cross direction of the sample and the receiver travels over the cross direction of the moving sample.

20. The sensor of claim 11 wherein the sample comprises paper, plastic or powdered products.

21. A method of measuring at least one property of a moving sample that comprises the steps of:
    (a) directing radiation from a light source at the moving sample;
    (b) measuring reflected or transmitted radiation from the sample with a receiver and generating electrical signals therefrom such that when the receiver is configured to measure transmitted radiation from the moving sample the light source and the receiver are positioned on opposite sides of the sample and the distance between the light source and the receiver varies and wherein step (b) comprises obtaining absorption as a function of time-of-flight measurements or comprises removing measurements caused by excessive scattering within the moving sample; and
    (c) determining at least one property of the moving sample from the electrical signals whereby electrical signals associated with scattering within the sample are processed with the consideration that scattered photons have longer transit times than those of non-scattered photons.

22. The method of claim 21 comprising the step of synchronizing steps (a) and (b).

23. A method of measuring at least one property of a moving sample that comprises the steps of:
    (a) directing radiation from a light source at the moving sample;
    (b) measuring reflected or transmitted radiation from the sample with a receiver and generating electrical signals therefrom such that when the receiver is configured to measure transmitted radiation from the sample the light source and the receiver are positioned on opposite sides of the sample and the distance between the light source and the receiver varies;
    (c) gating the electrical detection signals to eliminate signals outside a fixed time window relative to the synchronization pulses; and
    (d) determining at least one property of the sample from the electrical signals whereby electrical signals associated with scattering within the sample are processed with the consideration that scattered photons have longer transit times than those of non-scattered photons.

24. The method of claim 23 comprising the step of synchronizing steps (a) and (b).

* * * * *